Figure 1:
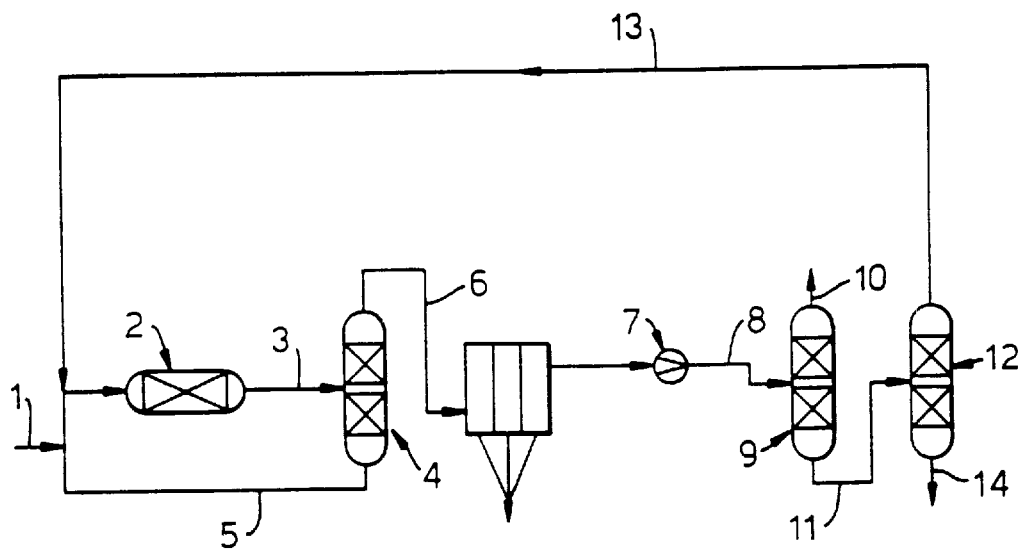

United States Patent [19]
Shields et al.

[11] Patent Number: 5,962,753
[45] Date of Patent: *Oct. 5, 1999

[54] PROCESS FOR THE MANUFACTURE OF PENTAFLUOROETHANE

[75] Inventors: Charles John Shields; Paul Nicholas Ewing, both of Warrington, United Kingdom

[73] Assignee: Imperial Chemical Industries PLC, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,169
[22] PCT Filed: Aug. 8, 1995
[86] PCT No.: PCT/GB95/01872
§ 371 Date: Feb. 18, 1997
§ 102(e) Date: Feb. 18, 1997
[87] PCT Pub. No.: WO96/06062
PCT Pub. Date: Feb. 29, 1996

[30] Foreign Application Priority Data

Aug. 24, 1994 [GB] United Kingdom .................. 9417116

[51] Int. Cl.$^6$ ............................. C07C 17/08; C07C 17/38
[52] U.S. Cl. ............................................. 570/169; 570/177
[58] Field of Search ...................................... 570/169, 177

[56] References Cited

FOREIGN PATENT DOCUMENTS

| 0 502 605 | 9/1992 | European Pat. Off. . |
| 901 297 | 7/1962 | United Kingdom . |
| 95 16654 | 6/1995 | WIPO . |
| WO 95/16654 | 6/1995 | WIPO . |

*Primary Examiner*—Alan Siegel

[57] ABSTRACT

Process for the manufacture of pentafluoroethane [HFC 125] by reaction of perchloroethylene with hydrogen fluoride in the vapor phase over a fluorination catalyst in a fluorination reactor with recycle of dichlorotrifluoroethane [HCFC 123] and chlorotetrafluoroethane [HCFC 124] to the fluorination reactor, wherein tetrafluoroethane [HFC 134*a*] is also recycled to the fluorination reactor. The tetrafluoroethane and the chlorotetrafluoroethane can both be separated from the product stream in a single distillation column and recycled, together to the fluorination reactor.

6 Claims, 1 Drawing Sheet

PROCESS FOR THE MANUFACTURE OF PENTAFLUOROETHANE

This application is a 371 of PCT/GB95/01872 filed Aug. 8, 1995.

This invention relates to a process for the manufacture of pentafluoroethane [HFC 125] and particularly to a process comprising the manufacture of pentafluoroethane by reacting perchloroethylene with hydrogen fluoride in the gas phase over a fluorination catalyst such as chromia. It has been proposed to manufacture pentafluoroethane for use as or as a component of refrigerant compositions by the hydrofluorination of perchloroethylene or dichloro-1,1,1-trifluoroethane [HCFC 123]. High conversions of perchloroethylene are attainable and the selectivity of the process to pentafluoroethane is acceptable. However, a number of intermediates and by-products are commonly produced and the product stream often contains one or more isomers of dichlorotetrafluoroethane [CFC 114/114a], dichlorotrifluoroethane [HCFC 123/123a], chlorotetrafluoroethane [HCFC 124/124a], chlorotrifluoroethane [HCFC 133/133a], tetrafluoroethane [HFC 134/134a] and chloropentafluoroethane [CFC 115] as well as unreacted hydrogen fluoride and by-product hydrogen chloride. Intermediate products such as HCFC 123 and HCFC 124 are readily separated from the product stream by distillation and can be recycled to the hydrofluorination reactor for further fluorination. HCFC 133a and HFC 134a are also readily separated from the pentafluoroethane product stream by distillation but these cannot be fluorinated to pentafluoroethane by recycling them to the hydrofluorination reactor so they are generally removed from the process.

The impurities in the organic product stream, which may be present in an appreciable amount, for example up to 10–20% by weight, range from low boiling compounds (or lights) to high boiling compounds (or heavies) relative to pentafluoroethane and their removal from the stream usually is effected sequentially in a series of distillation columns. Thus for example, the stream from the fluorination reactor may be fed to a first column from which hydrogen fluoride, dichlorotrifluoroethane [HCFC 123/123a] and other heavies are removed as a bottom fraction whilst the remainder of the stream is removed as a top fraction. The bottom faction from this first column may be recycled to the fluorination reactor.

The top fraction from the first column, optionally after aqueous scrubbing and drying, may be fed to a second distillation column from which pentafluoroethane [HFC 125] is withdrawn together with chloropentafluoroethane [CFC 115] as a top faction whilst the remainder of the stream, comprising mainly chlorotetrafluoroethane [HCFC 124/124a], chlorotrifluoroethane [HCFC 133/133a], tetrafluoroethane [HFC 134/134a] and dichlorotetrafluoroethane [CFC 114/144a] is withdrawn as a bottom fraction. The pentafluoroethane (containing chloropentafluoethane) withdrawn as a top fraction may be further treated to effect purification of the pentafluoroethane.

The bottom fraction from the second column may be fed to a third distillation column from which tetrafluoroethane [HFC 134/134a] is withdrawn as a top fraction and removed from the system whilst the remainder of the stream is withdrawn as a bottom fraction and passed to a fourth distillation column from which chlorotetrafluoroethane [HCFC 124/124a] is withdrawn as a top fraction whilst dichlorotetrafluoroethane [CFC 114/114a] and chlorotrifluoroethane [HCFC 133/133a] are withdrawn as a bottom fraction. The chlorotetrafluoroethane [HCFC 124/124a] may be recycled to the fluorination reactor for fluorination to pentafluoroethane [HFC 125]. The amounts of CFC 114/114a and HCFC 133/133a in the bottom fraction from the fourth column is usually so low that recovery of the components is not economic and the mixture is usually disposed of, for instance by thermal oxidation.

As stated above, aqueous scrubbing is optional. Where this step is excluded, the various top and bottom fractions from the columns may contain hydrogen fluoride in addition to the components recited and the various components may be in the form of azeotropes or azeotrope-like compositions with hydrogen fluoride.

According to the present invention there is provided a process for the manufacture of pentafluoroethane by reaction of perchloroethylene with hydrogen fluoride in the vapour phase over a fluorination catalyst in a fluorination reactor with recycle of dichlorotrifluoroethane and chlorotetrafluoroethane to the fluorination reactor wherein tetrafluoroethane is also recycled to the fluorination reactor.

In the fluorination reactor the recycled tetrafluoroethane [HFC 134/134a] reacts with hydrogen chloride produced in the reactor to form chlorotrifluoroethane [HCFC 133a]. As described hereinbefore, HCFC 133a is subsequently removed from the process (and usually is disposed of by thermal oxidation). Thus recycling tetrafluoroethane [HFC 134/134a] to the fluorination reactor results in removal of tetrafluoroethane from the process. Removal and recycling of the tetrafluoroethane together with chlorotetrafluoroethane in one distillation column reduces the number of columns required to treat the product stream from the fluorination reactor and in particular the need for a column dedicated to removal of tetrafluoroethane is obviated.

Figure 2:
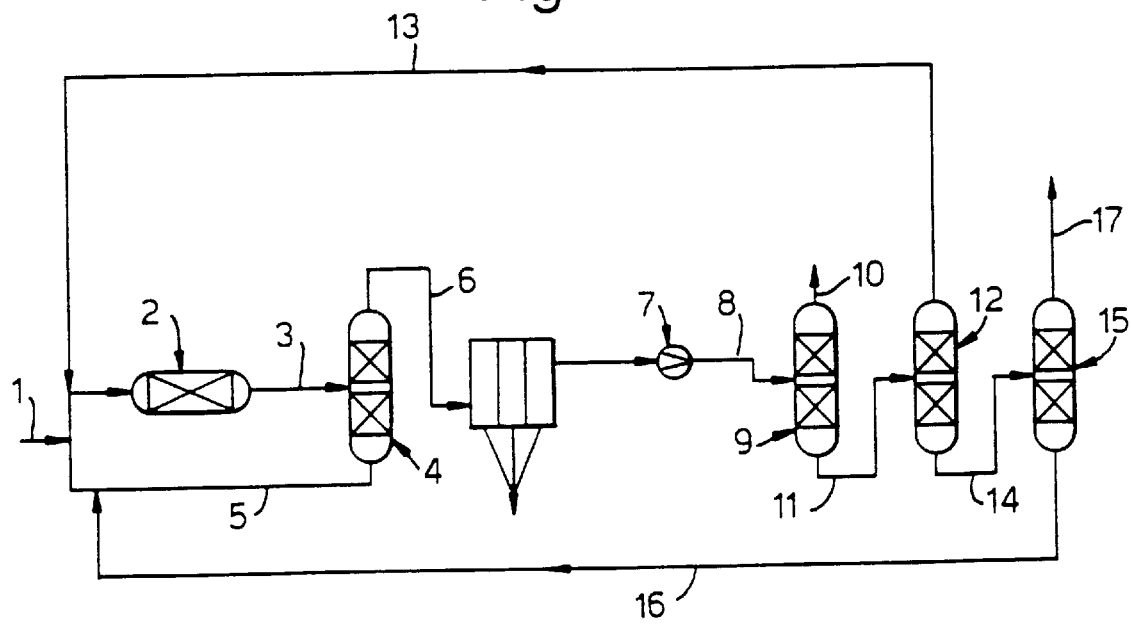

The invention will now be illustrated with reference to the drawings in which FIGS. 1 and 2 show flow sheets of processes in which tetrafluoroethane [HFC 134a] is separated together with chlorotetrafluoroethane [HCFC 124] and recycled to a fluorination reactor in which pentafluoroethane is produced by reaction of perchloroethylene with hydrogen fluoride. The difference between the processes is that in FIG. 1 the intermediate dichlorotetrafluoroethane [HCFC 123] is separated in a single distillation column whilst in FIG. 2 the HCFC 123 is separated in two distillation columns.

Referring to FIG. 1, perchloroethylene and hydrogen fluoride are fed as stream 1 to a fluorination reactor 2 containing a fluorination catalyst (for example chromia or zinc-promoted chromia) and heated at 200–400° C. The resulting product stream comprising pentafluoroethane and intermediates and impurities is fed via 3 to a first distillation column 4 operating at a pressure of 8–12 bar and temperature of 20–40° C. HCFC 123, hydrogen fluoride and other relatively high boiling compounds (heavies) are withdrawn from the bottom of column 4 via 5 and recycled to the fluorination reactor 2 together with the perchloroethylene and hydrogen fluoride fed via 1.

The remaining product stream withdrawn from the top of column 4 via 6 is scrubbed with water, dried and compressed at 7 and fed via 8 to a second distillation column 9 operating at a pressure of 2.5–20 bar and a temperature of −25 to +45° C. Pentafluoroethane [HFC 125] is withdrawn from the top of column 9 via 10 together with chloropentafluoroethane [CFC 115] and the remaining product stream is withdrawn from the bottom of the column via 11 and fed to a third distillation column 12. Column 12 is operated at a pressure of 1.6–20 bar and temperature of 0–70° C. and tetrafluoroethane [HFC 134a] is withdrawn from the top via 13 together with chlorotetrafluoroethane [HCFC 124]. The HFC 134a and HCFC 124 are recycled to the fluorination reactor 2 together with the HCFC 123, hydrogen fluoride and perchloroethylene.

Dichlorotetrafluoroethanes [CFC 114/114a] and chlorotrifluoroethane [HCFC 133a] are withdrawn from the bottom of column 12 and fed via 14 to e.g. a thermal oxidiser for disposal.

The process shown in FIG. 2 is similar to that shown in FIG. 1 except that the first distillation column 4 is operated to separate part only of the dichlorotrifluoroethane [HCFC 123]. In this case, the process includes a fourth distillation column 15 from which dichlorotrifluoroethane [HCFC 123] is withdrawn as a bottom fraction via 16 and is recycled to the fluorination reactor 2 whilst dichlorotetrafluoroethanes [CFC 114/114a] and chlorotrifluoroethane [HCFC 133a] are withdrawn as a top faction and fed via 17 to e.g. a thermal oxidiser.

In each of the processes illustrated in FIG. 1 and FIG. 2, tetrafluoroethane [HFC 134a] is converted to chlorotrifluoroethane [HFC 133a] in the fluorination reactor and the HCFC 133a is subsequently removed from the system so that HFC 134a is removed from the pentafluoroethane product stream without the need to provide a dedicated distillation column to effect the separation.

The overall effect of the process according to the invention is the removal of the 13* series products (HFC 134a and HCFC 133a) from the pentafluoroethane product stream, the technique relying on the conversion of HFC 134a to HCFC 133a by reaction with by-product hydrogen chloride in the fluorination reactor. A competing reaction in the fluorination reactor is the reaction of HCFC 133a with hydrogen fluoride to produce HFC 134a so that an alternative technique for removing the 13* series products from the pentafluoroethane product stream would be to remove the HFC 134a from the system and recycle the HCFC 133a. However, this alternative technique suffers from the disadvantage that a large volume of HCFC 133a has to be recycled. The fluorination of HCFC 133a to produce HFC 134a is equilibrium–limited and under typical operating conditions to make HFC 125, the conversion of HCFC 133a to HFC 134a is only about 5% per pass through the fluorination reactor and a large volume of HCFC 133a has to be recycled. It is estimated that in practice this alternative technique for removing the 13* series products would involve a recycle stream in which HCFC 133a is one of the major components and accounts for up to a third or more of the recycle stream. By contrast, the technique according to the invention involves the recycle of an extremely small volume of HFC 134a. Minimising the volume of the recycle stream is a further advantage provided by the process according to the invention.

The above description of the invention with reference to the drawings includes a guide as to the operating conditions for the fluorination reactor and distillation columns used to produce and treat the pentafluoroethane product stream but it is to be understood that this is by way of a guide only. The operating conditions are well known in the art. The catalyst in the fluorination reactor typically will be and preferably is a chromia-based catalyst.

In the preferred embodiment of the process according to the invention, the tetrafluoroethane is removed from the product stream and recycled together with the HCFC 124. It is a simple matter to determine the optimum operating conditions for a distillation column to effect the removal of both HFC 134a and HCFC 124, optionally together with hydrogen fluoride. As a guide typical operating conditions are a superatmospheric pressure of from 2 to 8 bars and a temperature of 0° C. to 50° C. but it will be appreciated that operation under these conditions is not an essential feature of the invention.

We claim:

1. A process for the manufacture of pentafluoroethane by reaction of perchloroethylene with hydrogen fluoride in the vapour phase over a fluorination catalyst in a fluorination reactor with recycle of dichlorotrifluoroethane and chlorotetrafluoroethane to the fluorination reactor, characterised in that tetrafluoroethane is also recycled to the fluorination reactor, wherein tetrafluoroethane is converted into chlorotrifluoroethane by reaction with hydrogen chloride produced in the reactor.

2. A process as claimed in claim 1 wherein the tetrafluoroethane is separated from the pentafluoroethane product stream and recycled together with the chlorotetrafluoroethane.

3. A process as claimed in claim 2 wherein the separation of the tetrafluoroethane and the chlorotetrafluoroethane from the product stream is effected in a single distillation column.

4. A process as claimed in claim 3 wherein the distillation column is operated at a pressure of from 1.6 to 20 bar.

5. A process as claimed in claim 3 wherein the distillation column is operated at a temperature of from 0° C. to 70° C.

6. A process as claimed in claim 1 wherein the fluorination catalyst is a chromia-based catalyst.

* * * * *